United States Patent [19]

Spiller

[11] Patent Number: 4,728,325

[45] Date of Patent: Mar. 1, 1988

[54] DIAPER BACKSHEET

[75] Inventor: Russell A. Spiller, Crystal Lake, Ill.

[73] Assignee: Exxon Chemical Patents Inc., Linden, N.J.

[21] Appl. No.: 849,074

[22] Filed: Apr. 3, 1986

[51] Int. Cl.$^4$ .................. A61F 13/16; A61F 13/18; A61F 13/20

[52] U.S. Cl. .................. 604/372; 604/385 R; 604/389; 524/240

[58] Field of Search ........... 524/240; 604/372, 381, 604/375, 378, 385, 389

[56] References Cited

U.S. PATENT DOCUMENTS

| | | | |
|---|---|---|---|
| 2,868,762 | 1/1959 | Oakes | 525/240 |
| 3,125,548 | 3/1964 | Anderson | 525/240 |
| 3,179,719 | 4/1965 | Clines | 525/240 |
| 3,230,288 | 1/1966 | Henderson | 525/240 |
| 3,783,871 | 1/1974 | Sabee | 604/372 |
| 3,998,914 | 12/1976 | Lillis et al. | 525/240 |
| 4,230,831 | 10/1980 | Sakurai et al. | 525/240 |
| 4,298,722 | 11/1981 | Collette et al. | 525/240 |
| 4,346,834 | 8/1982 | Mazumdar | 525/240 |
| 4,367,841 | 1/1983 | Mazumdar | 525/240 |
| 4,381,781 | 5/1983 | Sciaratta et al. | 604/372 |
| 4,436,520 | 3/1984 | Lipko et al. | 604/385.1 |
| 4,614,764 | 9/1986 | Colombo et al. | 525/240 |

FOREIGN PATENT DOCUMENTS

| | | | |
|---|---|---|---|
| 2056996 | 3/1981 | United Kingdom | 525/240 |
| 2148906 | 6/1985 | United Kingdom | 525/240 |

*Primary Examiner*—C. Fred Rosenbaum
*Assistant Examiner*—Jerome R. Smith, Jr.
*Attorney, Agent, or Firm*—C. E. Smith

[57] ABSTRACT

Adhesion to a low gloss polyolefin surface is improved by forming the polyolefin from linear low density polyethylene (LLDPE) with hexene-1 as the comonomer, particularly LLDPE with a density of less than 0.926 and high pressure low density polyethylene (LDPE density of 0.910-0.925) or a mixture of the high pressure low density polyethylene and up to 30 wt. % of a high density polyethylene (HDPE density 0.948-0.965). Preferably the polyolefin composition will contain 45 to 85 wt. % of the LLDPE and 10 to 60 wt. % of LDPE.

7 Claims, No Drawings

DIAPER BACKSHEET

BACKGROUND OF THE INVENTION

1. Field of the Invention

The present invention relates to matte finish, i.e., non-shiny polyethylene films, for example, embossed films having improved tape adhesion. More particularly, the invention concerns linear low density polyethylene containing a specific comonomer for use in low gloss surface applications.

2. Related Art

Many applications of polyethylene films require a low gloss surface. That is the surface may be embossed or patterned for aesthetic or useful reasons. For example, one utilization where a reduced gloss finish is required is on the back sheet of a disposable diaper. Disposable diapers are conventionally constructed of an absorbent inner layer disposed between a non-woven permeable top sheet and a film back sheet having closure tabs to secure the diaper in place.

The back sheet (outer sheet) may be embossed in order to reduce the gloss to an acceptable level. Embossing or other methods of reducing surface gloss also materially reduce the adhesion of the reduced gloss surface for the closure tabs thereby causing the diaper to be insecure in use, that is, the tabs may peel and release the diaper from an infant.

There are various methods which may recover or improve the lost adhesion of the tabs to the back sheet, such as longer adhesive tabs, tackier adhesives, corona discharge treatment of the back sheet film and careful control of the profile of the embossed surface, the latter being disclosed in U.S. Pat. No. 4,436,520.

The present invention provides the advantage that ordinary embossing or surface matting procedures may be employed with improved tab adhesion. It is also an advantage that the present invention does not cause a problem with handling of the back sheet stock manufacture. For example, light corona treatment to enhance the peel force could result in film roll blocking during unwinding. It is a particular feature that the improved tab adhesion of the present invention does not require a separate process step such as corona discharge. Hence it is a feature of the present invention that a very specific type of polyolefin film material is used for the low gloss films to have improved adhesion properties on low gloss surfaces. These and other advantages and features will become apparent from the following disclosure.

SUMMARY OF THE INVENTION

Briefly, the present invention is the discovery that low gloss films of specific linear low density polyethylene (LLDPE), wherein the LLDPE is prepared by a gas phase process with hexene comonomer, have improved adhesion on the low gloss surface. Basically the films comprise from 30 to 95 wt. % LLDPE preferably 40 to 90 wt. % and more preferably 45 to 85 wt.% LLDPE and from 5 to 70 wt.%, preferably from 10 to 60 wt. % high pressure low density polyethylene (LDPE) or a mixture thereof with up to 30 weight high density polyethylene (HDPE). In addition to these components the films may contain conventional UV stabilizers, plasticers, flame retardants, antioxidants and the like. Preferred films comprise LLPDE and LDPE as the polyethylene component. The LLDPE contains as the copolymer up to about 20% hexene-1, preferably about 3 to 16 wt.% hexene-1, most preferably 6 to 14 wt.% hexene-1.

In accordance with this invention there is also provided a disposable diaper having a back sheet, an absorbent inner layer, non woven top sheet and adhesive closure tabs made of a polyolefin tape such as polypropylene provided with an adhesive, wherein the exposed surface of the back sheet is a low gloss surface, preferably embossed, said back sheet comprising a polymer as described above.

The term low gloss as used herein means a 45° gloss of no greater than 9, preferably less than 8. The linear low density polyethylene will have a density less than 0.930 and more preferably less than 0.926, specifically less than about 0.920 to about 0.900, preferably to about 0.910 while the high pressure low density polyethylene homopolymers will have densities generally in the range of 0.910–0.925. High density polyethylenes generally are those having densities in the range of 0.941 to 0.965.

Percentages are by weight unless otherwise stated the weight percentages of the polyolefin compositions are based on the total composition.

DETAILED DESCRIPTION OF THE INVENTION

LLDPE (linear low density polyethylene) is produced by copolymerizing ethylene with a $C_4$ to $C_{10}$ alpha-olefin. Generally in the prior art preferred alpha-olefins include those selected from the group comprising butene-1, pentene-1, hexene-1, 4 methylpentene-1, heptene-1, and octene. However, it has been found that for the present invention LLDPE comprising hexene-1 and produced by the gas phase process provides the improved adhesion other comonomers do not. The comonomers are present in amounts up to 20 wt.%, normally between 3 and 14 wt.%. The polymerization is at low pressure conducted using a chromium catalyst or Ziegler catalyst and may be carried out by gas phase. The LLDPE produced by these methods have a density between 0.900 and 0.935 g/cm$^3$ with the present LLDPE compositions having densities of less than 0.930; Mw/Mn ratio of 3 to 15 and an MI between 0.1 and 5.0 grams per 10 minutes. Manufacturing processes for LLDPE are disclosed in U.S. Pat. Nos. 4,076,698 and 4,205,021.

A preferred LLDPE is produced by gas phase process at 150–300 psi and temperatures of 80° to 95° C. The product may be used in granular form or pelletized. This material is then blended with any other polymeric or blend component by one of the methods known to the art. It is important that very thorough blending and uniform polymer blend be obtained. Various methods which may be used are dry blending or melt blending.

In addition to the LLDPE the films may contain high pressure, low density polyethylene (LDPE) or high pressure ethylene copolymers such as EVA (1–15% VA), or mixtures thereof with high density polyethylene which may both be generally produced at around 3,000 atmospheric at 80° to 300° C. in well known and conventional procedures. The polymeric film or sheets formed from the specified resin may be produced by conventional means, such as extrusion through a slot die or by casting techniques.

Embossing is typically used on the surface of the polyolefin film to reduce gloss. A gloss of 8 or less is generally required for commercial acceptance of the film. Embossing can be imposed on the film surface by an embossing roll at the time of the film fabrication or at a subsequent time by procedures well known in the art.

The reason as to why the film of the specific composition claimed in the present invention are superior to other films generally and to closely related LLDPE films has not been fully discerned.

The following examples are submitted to illustrate the invention and are not intended to limit the scope thereof.

EXAMPLE 1

Six different LLDPE grades (densities) were evaluated on a Killian cast line. Two levels of LLDPE loadings (50 wt.% and 80 wt.%) were used for extrusion. Each film contained the specified LLDPE at 50 wt.% or 80 wt.%, 6% of a commercial color concentrate, with the balance being LDPE of MI 12 (Exxon Chemicals USA grade LD-202). TABLE I shows tape peel force (TPF) test results.

The TPF test was carried out on the chill roll side only. The TPF was carried out according to a test which measured the force in grams to peel the closure tape with adhesive from the film. The test is such that tape peel forces greater than 600 grams are required for desired diaper performance. The gloss was the measurement of a stack of film 10 layers thick using a Gardner Digital Photometric Unit PG 5500, Gardner Instruments, Bethesda, Md.

TABLE I

| Sample # | LLDPE Density | Comonomer | Wt. % | Tape Peel Force g |
|---|---|---|---|---|
| 1 | .918 | Butene | 50% | 553 |
| 2 | .918 | Butene | 80% | 587 |
| 3 | .918 | Hexene | 50% | 903+ |
| 4 | .918 | Hexene | 80% | 858 |
| 5 | .918 | Octene | 50% | 579 |
| 6 | .918 | Octene | 80% | 550 |
| 7 | .926 | Hexene | 50% | 560 |
| 8 | .926 | Hexene | 80% | 691 |
| 9 | .935 | Butene | 50% | 564 |
| 10 | .935 | Butene | 80% | 521 |
| 11 | .935 | Octene | 50% | 499 |
| 12 | .935 | Octene | 80% | 514 |

EXAMPLE 2

A set of runs was carried out with embossed film prepared from LLDPE, LDPE and HDPE over a range of compositions. The LLDPE employed had a density of 0.918 with 9 wt.% hexene comonomer. The LDPE had a density of 0.918 and the HDPE had a density of 0.952. The compositions are set out in TABLE II.

TABLE II

| | MICROPATTERN/TRI-BLEND SAMPLE # | | | | |
|---|---|---|---|---|---|
| COMPOSITION | 1/2 | 3/4 | 5/6 | 7/8 | 9/10 |
| LLDPE | 80 | 50 | 50 | 50 | 20 |
| HDPE | 0 | 30 | 15 | 0 | 30 |
| LDPE | 13 | 13 | 28 | 43 | 43 |
| COLOR CONCENTRATE | 7 | 7 | 7 | 7 | 7 |

The embossing was obtained with a wet rubber roll. The TPF Test was carried out on the chill roll side of the film. TPF and gloss are reported in TABLE III.

TABLE III

| Sample | Wt. %, Composition* LLDPE | LDPE | HDPE | Chill Roll, °C. | Gloss | TPF, g |
|---|---|---|---|---|---|---|
| 1 | 80 | 13 | 0 | 80 | 6.5 | 686 |
| 2 | 80 | 13 | 0 | 150 | 8.7 | 781 |
| 3 | 50 | 13 | 30 | 150 | 6.3 | 620 |
| 4 | 50 | 13 | 30 | 80 | 6.2 | 633 |
| 5 | 50 | 28 | 15 | 80 | 5.7 | 616 |
| 6 | 50 | 28 | 15 | 150 | 6.5 | 662 |
| 7 | 50 | 43 | 0 | 150 | 8.1 | 694 |
| 8 | 50 | 43 | 0 | 80 | 6.1 | 623 |
| 9 | 20 | 43 | 30 | 80 | 5.5 | 552 |
| 10 | 20 | 43 | 30 | 150 | 6.6 | 536 |

EXAMPLE 3

For comparison a LDPE (0.924 density was prepared with a surface of smooth to fairly rough and subjected to the Tape Peel Force test. The results are shown in TABLE IV, demonstrating pattern has little effect on TPF.

TABLE IV

| Sample | Pattern Roll Roughness (micro inches) | TPF, g |
|---|---|---|
| 1 | 44 | 450 |
| 2 | 40 | 460 |
| 3 | 25 | 470 |
| 4 | smooth | 490 |

The invention claimed is:

1. A disposable diaper having a diaper backsheet of polyolefin, a non-woven top sheet, an absorbent inner layer and refastenable adhesive closure tabs, said polyolefin backsheet having a 45° gloss of less than 9 and a tape peel force greater than 600 grams on the surface exposed to said adhesive tabs, said polyolefin comprising from 30 to 95 wt.% linear low density polyethylene containing hexene-1 comonomer in an amount up to 20 wt.% and from 5 to 70 wt.% of a low density polyethylene or a mixture of low density polyethylene and up to 30 wt.% high density polyethylene.

2. The disposable diaper according to claim 1 wherein said linear low density polyethylene contains 6 to 12 wt.% hexene-1 and has a density of less than 0.930, said low density polyethylene has a density in the range of 0.910 to 0.925 and said high density polyethylene has a density in the range of 0.941 to 0.965.

3. The disposable diaper according to claim 2 comprising 40 to 90 wt.% of said linear low density polyethylene and from 10 to 60 wt.% of said low density polyethylene.

4. The disposable diaper according to claim 3 comprising from 45 to 85 wt.% of said linear low density polyethylene having a density in the range of 0.910 to 0.920.

5. The disposable diaper according to claim 4 wherein said exposed surface has a 45° gloss of no greater than 8.

6. The disposable diaper according to claim 4 wherein said low gloss exposed surface is embossed.

7. The disposable diaper according to claim 1 wherein the surface for contacting the closure tabs is embossed and has an adhesive force of at least 10% higher than the film composition comprising of LDPE, HDPE, LLDPE (butane copolymer) or mixtures of these.

* * * * *